US009999355B2

(12) United States Patent
Kirenko

(10) Patent No.: US 9,999,355 B2
(45) Date of Patent: Jun. 19, 2018

(54) DEVICE, SYSTEM AND METHOD FOR DETERMINING VITAL SIGNS OF A SUBJECT BASED ON REFLECTED AND TRANSMITTED LIGHT

(71) Applicant: KONINKLIJKE PHILIPS N.V., Eindhoven (NL)

(72) Inventor: Ihor Olehovych Kirenko, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 595 days.

(21) Appl. No.: 14/615,531

(22) Filed: Feb. 6, 2015

(65) Prior Publication Data

US 2015/0223700 A1 Aug. 13, 2015

Related U.S. Application Data

(60) Provisional application No. 61/938,919, filed on Feb. 12, 2014.

(51) Int. Cl.
*A61B 5/00* (2006.01)
*A61B 5/0205* (2006.01)
(Continued)

(52) U.S. Cl.
CPC .......... *A61B 5/0205* (2013.01); *A61B 5/0077* (2013.01); *A61B 5/02416* (2013.01);
(Continued)

(58) Field of Classification Search
CPC ... A61B 5/0205; A61B 5/0077; A61B 5/6825; A61B 5/02416; A61B 5/7278; A61B 5/0816; A61B 5/6892; A61B 2503/045
See application file for complete search history.

(56) References Cited

U.S. PATENT DOCUMENTS 7,376,451 B2 5/2008 Mahoney et al.
2007/0100219 A1 5/2007 Sweitzer et al.
(Continued)

FOREIGN PATENT DOCUMENTS

DE 19741982 A1 10/1998
WO 2013027141 A2 2/2013
(Continued)

OTHER PUBLICATIONS

Humphreys, K., et al.; A CMOS Camera-Based Pulse Oximetry Imaging System; 2005; IEEE EMBS; vol. 4:3494-3497.
(Continued)

*Primary Examiner* — Joel Lamprecht

(57) ABSTRACT

A device, system and method for determining vital signs of a subject is presented that improves accuracy and reliability, the device comprising a detection unit for contactless detection of light in at least two different wavelength ranges from a region of interest of a subject, wherein said detection unit is configured to detect a first light portion in a first wavelength range from light reflected from said region of interest in response to illumination by a first light source and to detect a second light portion in a second wavelength range from light transmitted through said region interest in response to illumination by a second light source, wherein said detection unit is configured to detect said first light portion and said second light portion simultaneously in response to illuminations that are at least temporarily simultaneous and wherein said first wavelength range and said second wavelength range are different. A processing unit is provided for deriving plethysmography, PPG, signals from the detected light for said at least two different wavelength ranges. An analysis unit is provided for deriving a desired vital sign from the PPG signals for at least two different wavelength ranges.

20 Claims, 4 Drawing Sheets

(51) Int. Cl.
    *A61B 5/024*     (2006.01)
    *A61B 5/08*     (2006.01)
    *A61B 5/1455*     (2006.01)

(52) U.S. Cl.
    CPC ........ *A61B 5/0816* (2013.01); *A61B 5/14551* (2013.01); *A61B 5/6825* (2013.01); *A61B 5/7278* (2013.01); *A61B 5/6815* (2013.01); *A61B 5/6892* (2013.01); *A61B 2503/045* (2013.01)

(56) References Cited

U.S. PATENT DOCUMENTS

| | | |
|---|---|---|
| 2008/0194906 A1 | 8/2008 | Mahoney et al. |
| 2010/0280348 A1* | 11/2010 | Wenzel ................ A61B 5/0452 600/365 |
| 2012/0108928 A1* | 5/2012 | Tverskoy ............. A61B 5/0059 600/324 |
| 2012/0203080 A1 | 8/2012 | Kim et al. |
| 2013/0066172 A1 | 3/2013 | Kulcke |
| 2013/0261415 A1 | 10/2013 | Ashe et al. |
| 2014/0031696 A1 | 1/2014 | Schmeitz et al. |
| 2014/0180136 A1* | 6/2014 | Su ...................... A61B 5/7221 600/479 |
| 2014/0205165 A1* | 7/2014 | Jeanne ................ A61B 5/1171 382/128 |
| 2015/0105670 A1 | 4/2015 | Bresch et al. |

FOREIGN PATENT DOCUMENTS

| | | |
|---|---|---|
| WO | 2013166341 A1 | 11/2013 |
| WO | 2013186696 A1 | 12/2013 |

OTHER PUBLICATIONS

Humphreys, K., et al.; Noncontact simultaneous dual wavelength photoplethysmography: A further step toward noncontact pulse oximetry; 2007; Review of Scientific Instruments; 78:044304.

Verkruysse, W., et al.; Remote plethysmographic imaging using ambient light; 2008; Opt. Express; 16(26) 21434-21445.

Wieringa, F. P., et al.; Contactless Multiple Wavelength Photoplethysmographic Imaging: A First Step Toward SpO2 Camera Technology; 2005; Annals of Biomedical Engineering; 33(8)1034-1041.

* cited by examiner

DEVICE, SYSTEM AND METHOD FOR DETERMINING VITAL SIGNS OF A SUBJECT BASED ON REFLECTED AND TRANSMITTED LIGHT

CROSS REFERENCE TO RELATED APPLICATIONS

This application claims the benefit of U.S. provisional application Ser. No. 61/938,919 filed Feb. 12, 2014 and EP provisional application serial no. 14154890.9 filed Feb. 12, 2014, which are incorporated herein by reference.

FIELD OF THE DISCLOSURE

The present disclosure relates to a device, system and method for determining vital signs of a subject, such as a person or animal. Further, the present invention relates to a wearable light source device.

BACKGROUND OF THE DISCLOSURE

Vital signs of a person, for example the heart rate (HR), the respiration rate (RR) or the arterial blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heartbeat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Conventional pulse oximeters (also called contact PPG device herein) for measuring the heart rate and the (arterial) blood oxygen saturation (also called SpO2) of a subject are attached to the skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmittance of the same area or volume of tissue at two different wavelengths. This is referred to as time-division-multiplexing. The transmittance over time at each wavelength gives the PPG waveforms for red and infrared wavelengths. Although contact PPG is regarded as a basically non-invasive technique, contact PPG measurement is often experienced as being unpleasant and obtrusive, since the pulse oximeter is directly attached to the subject and any cables limit the freedom to move and might hinder a workflow.

Fast and reliable detection and analysis of a pulse signal and oxygen saturation level (SPO2) is one of the most important activities in many healthcare applications, which becomes crucial if a patient is in a critical condition. In those situations, pulsatility of a heartbeat signal is very weak, and therefore, the measurement is vulnerable to any sort of artifacts.

Modern photoplethysmography sensors do not always provide fast and reliable measurement in critical situations. For instance, contact finger pulse oximeters (based on transmissive PPG) are vulnerable to motion of a hand, and fails in case of centralization of a patient due to lower blood volumes on body peripherals. Contact forehead pulse oximeter sensors (using a reflective PPG measurement mode) are supposed to be more robust to a centralization effect. However, the accuracy, robustness and responsiveness of a forehead sensor depends heavily on correct positioning of a sensor on a forehead and proper pressure applied to a skin (too tight application of a sensor might reduce a local blood pulsatility, too loose application might lead to non-reliable measurements due to motion artifacts and/or venous pulsatility).

Recently, non-contact, remote PPG (rPPG) devices (also called camera rPPG device herein) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue colour channels.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Using PPG technology, vital signs can be measured, which are revealed by minute light absorption changes in the skin caused by the pulsating blood volume, i.e. by periodic color changes of the human skin induced by the blood volume pulse. As this signal is very small and hidden in much larger variations due to illumination changes and motion, there is a general interest in improving the fundamentally low signal-to-noise ratio (SNR). There still are demanding situations, with severe motion, challenging environmental illumination conditions, or high required accuracy of the application, where an improved robustness and accuracy of the vital sign measurement devices and methods is required, particularly for the more critical healthcare applications.

US 2008/0194906 A1 discloses a non-intrusive physiological data measurement system and method, as well as an optically induced treatment system. The measurement system includes a monitoring mechanism that includes light emitter modules capable of emitting light at least two wavelengths. The light emitted from the light emitter modules is transmitted through a subject and to a light receiving mechanism, such as an optical sensor. Physiological data is taken from the received light. The system also can ascertain movement of the subject by obtaining an initial outline of the subject and comparing that outline with a subsequently obtained outline. A therapeutic optic system includes a non-adhering light emitting mechanism for providing light at therapeutic wavelengths.

SUMMARY OF THE DISCLOSURE

It an object of the present disclosure to provide an improved device, system and method for determining vital signs of a subject having an increased signal-to-noise ratio and efficiency in reduction of artefacts caused by distortions, in particular by motion of the subject or disturbance from ambient light. It is a further object of the present invention to provide a corresponding wearable light source device for use in such a system and method.

In a first aspect of the present disclosure a device for determining vital signs of a subject is presented, the device comprising:
 a detection unit configured for contactless detection of light in at least two different wavelength ranges from a region of interest of a subject, wherein said detection unit is configured to detect a first light portion in a first wavelength range from light reflected from said region of interest in response to illumination by a first light source and to detect a second light portion detected in a second wavelength range from light transmitted through said region interest in response to illumination by a second light source, wherein said detection unit is configured to detect said first light portion and said second light portion simultaneously in response to illuminations that are at least temporarily simultaneous and wherein said first wavelength range and said second wavelength range are different,
 a processing unit configured to deriving plethysmography, PPG, signals from the detected light for said at least two different wavelength ranges, and
 an analysis unit configured to derive a desired vital sign from the PPG signals for at least two different wavelength ranges.

In a further aspect of the present disclosure a corresponding method is presented.

In still a further aspect of the present disclosure a system for determining vital signs of a subject is presented, the system comprising:
 a device for determining vital signs of a subject as disclosed herein,
 a light source (also sometimes referred to as second light source hereafter) configured to transmit light through a region interest of a subject for illuminating the region of interest to obtain transmitted light, wherein the transmission of light and the illumination of the subject by light to obtain reflected light are at least temporarily simultaneous.

Preferred embodiments of the disclosure are defined in the dependent claims. It shall be understood that the claimed method and system have similar and/or identical preferred embodiments as the claimed device and as defined in the dependent claims.

The present disclosure is based on the following findings. A classical embodiment of a vital signs camera (i.e. a device for determining vital signs of a subject) for remote PPG uses a reflective method of measurement of PPG signal, where an ambient or dedicated illumination is used. Although such reflective remote PPG technique is the most convenient, in cases of severe disturbance from ambient illumination, or if a pulsatility of a PPG signal is very low, SNR of the extracted signal will be weak and the measurements would be vulnerable to artifacts. The reason for this is the fact that pulsatility of a PPG signal measured in reflective mode is lower, than the one measured in a transmissive mode, due to a smaller penetration depth of a light in a reflective mode. Especially, pulsatility of a PPG signals measured in red and infrared color range using remote reflective PPG approach might be very low, thus reducing an accuracy of SPO2 measurement.

The present disclosure overcomes the limitations of contactless camera-based reflective PPG technique and classical contact sensors by combining the advantages of transmissive mode for PPG signal acquisition and contactless sensing using a common detector, such as a camera. The disclosure thus makes use of advantages of a large sensing area, achieved with (particular camera-based) measurements in reflective mode, and a relatively large SNR of a PPG signal extracted in a transmissive mode.

According to the present disclosure a single detector (e.g. image sensor or camera) measures reflected and transmitted light simultaneously, and PPG signals are extracted from both reflected and transmitted illumination. The wavelengths of transmitted and reflected light used for evaluation and derivation of vital signs are complementary (e.g. green and red wavelengths are used from the reflected light, IR wavelengths are used from the transmitted light). Thus, evaluated wavelengths in transmissive and reflective modes are different. One or more vital signs may then be obtained with higher accuracy and robustness from the original PPG signal or one or more combined PPG signals.

The transmitted and reflected light may be obtained from the same or from different regions of interest (ROIs). For instance, for HR measurement, an acquisition of reflected (e.g. at green wavelength) and transmitted (in IR range) PPG signals is possible and useful. For SpO2, it is preferred to know the calibration constants for various body locations used for reflective PPG. Thus, calibration constants used for SPO2 calculations for the case when both reflective and transmissive PPG come from the same ROI and for the case when they are measured from different locations would be different. Generally, however, the transmitted PPG signals and the reflective PPG signal may be obtained from different ROIs or from the same ROI.

Generally, the interaction of electromagnetic radiation, in particular light, with biological tissue is complex and includes the (optical) processes of (multiple) scattering, backscattering, absorption, transmission and (diffuse) reflection. The term "reflect" as used in the context of the present disclosure is not to be construed as limited to specular reflection but comprises the afore-mentioned types of interaction of electromagnetic radiation, in particular light, with tissue and any combinations thereof.

The term "vital sign" as used in the context of the present disclosure refers to a physiological parameter of a subject (i.e. a living being) and derivative parameters. In particular, the term "vital sign" comprises blood volume pulse-signal, heart rate (HR) (sometimes also called pulse rate), heart rate variability (pulse rate variability), pulsatility strength, perfusion, perfusion indicator, perfusion variability, Traube Hering Mayer waves, respiratory rate (RR), skin temperature, blood pressure, a concentration of a substance in blood and/or tissue, such as (arterial) blood oxygen saturation or glucose level. Furthermore, "vital sign" generally includes health indications obtained from the shape of the PPG signal (e.g. shape may say something about partial arterial blockage (e.g. shape obtained from PPG signals of the hand gets more sinusoidal when applying a blood-pressure cuff on the arm), or about the skin thickness (e.g. a PPG signal from the face is different than from the hand), or maybe even about the temperature, etc.).

The term "vital sign information" as used in the context of the present disclosure comprises the one or more measured vital signs as defined above. Furthermore, it comprises data referring to a physiological parameter, corresponding waveform traces or data referring to a physiological parameter of a time that can serve for subsequent analysis.

For obtaining a vital sign information signal of the subject the data signals of skin pixel areas within the skin area are evaluated. Here, a "skin pixel area" means an area comprising one skin pixel or a group of adjacent skin pixels, i.e. a data signal may be derived for a single pixel or a group of skin pixels.

In an embodiment the device further comprises a control unit configured to control said first light source, said second light source and/or said detection unit to synchronize two or more of them with each other. For instance, the second light source may be controlled with the first light source and the detection unit such that only in each second sample of the detection signal transmitted light is measured, but each sample of the detection signal measures reflected light. This improves robustness of the finally obtained vital signs.

This embodiment of time sequential wavelength is applicable for two scenarios. First, when the system needs to decouple the contribution of the second light source from the contribution of an ambient light in the same range. Thus, for each wavelength, the detection unit will measure at even frames the mixture of the dedicated light and ambient light, and on odd frames the contribution of an ambient light only. By taking the difference between two adjacent frames (assuming the frame rate is sufficiently high), the contribution of only the second light source is measured. Second, this embodiment is useful also for another scenario, when a monochrome camera sensor is used as detection unit, which does not have optical filters to differentiate contributions from light sources at different wavelengths. In this scenario the proposed system simulates the behavior of a time sequential multispectral camera.

In another embodiment the device further comprises a control unit configured to control said first light source to emit light in said first wavelength range and/or said second light source to emit light in said second wavelength range. Generally, the first and/or second light source may be designed to emit light at only the first or second wavelength range, respectively. It is, however, preferred to control said wavelength ranges. This, for instance, enables using a single light source (e.g. as second light source) for alternately switching between different wavelength ranges (e.g. between red and infrared wavelength ranges or between two different infrared wavelength ranges).

In another embodiment said detection unit comprises one or more optical filters configured to filter light at one or more wavelength ranges out of the detected light. This further improves the accuracy and reliability of obtained vital signs.

Still further, in an embodiment the device further comprises a control unit configured to control said second light source to emit light in said one or more wavelength ranges, in particular in the red and infrared wavelength range, continuously. This is particularly preferred, if the detection unit comprises one or more filters.

The analysis unit is preferably configured for combining said PPG signals for at least two different wavelength ranges and deriving a desired vital sign from the combined PPG signals. There are different options for combining the PPG signals. For instance, an average may be combined of several PPG signals, or PPG signals in the red and infrared wavelength range are used to obtain the oxygen saturation of arterial blood in the generally known manner.

Advantageously, said detection unit is a camera for acquiring a set of image frames of the region of interest. From said image frames the PPG signals can then be extracted. Depending on the desired application, in particular the desired vital signs, a monochrome camera, an RGB camera or a special camera (e.g. optimized for acquisition of certain wavelength ranges) may be used.

The proposed system preferably comprises a first and second light source, e.g. dedicated lamps, for emitting the desired light. Preferably, one or more LEDs are used for this purpose.

The second light source is preferably configured for being arranged behind an ear, similar to a hearing aid to transmit light through the outer part of the ear, or on one side of a hand of a person to transmit light through the hand.

In another embodiment the system further comprises a neonatal intensive care unit (NICU) having a bottom layer, in particular a mattress, wherein said second light source comprises a plurality of light elements, in particular LEDs, arranged in said bottom layer. This enables to unobtrusively and continuously obtaining vital signs of a neonate in a reliable manner.

According to another aspect of the present invention a wearable light source device is presented, which may be used in the disclosed system and method, said device comprising:
 a holder for arranging the wearable light source device to a portion of a subject's body, in particular behind an ear or on one side of a hand of a person,
 a light source for emitting light, wherein the light source is mounted in or at the holder such that the emitted light is transmitted through a region interest of the subject for illuminating the region of interest to obtain transmitted light, and
 a control input for receiving control information for controlling the light source.

Preferably, said control input is configured for wirelessly receiving control information.

BRIEF DESCRIPTION OF THE DRAWINGS

These and other aspects of the disclosure will be apparent from and elucidated with reference to the embodiments described hereinafter. In the following drawings

DETAILED DESCRIPTION OF THE DISCLOSURE

Figure 1:
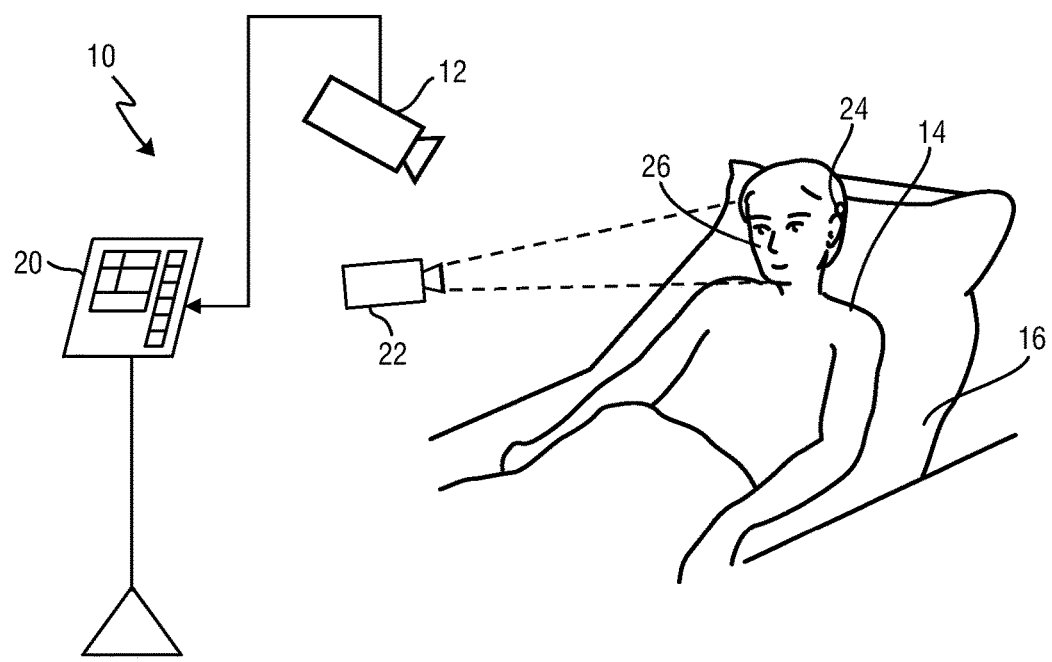
FIG. 1 shows a schematic diagram of a system including a device according to the present disclosure.

FIG. 1 shows a schematic diagram of a an embodiment of a system 10 including a device 12 for obtaining vital signs of a subject 14 according to the present disclosure. The subject 14, in this example a patient, lies in a bed 16, e.g. in a hospital or other healthcare facility, but may also be a neonate or premature infant, e.g. lying in an incubator, or person at home or in a different environment. Image frames of the subject 14 are captured by means of a camera (also referred to as detection unit or as camera-based or remote PPG sensor) including a suitable photosensor. The camera forwards the recorded image frames to processing means of the device 12, where the image frames will be process as explained in more detail below. The device 12 is further connected to an interface 20 for displaying the determined information and/or for providing medical personnel with an interface to change settings of the device 12 and/or other elements of the system 10. Such an interface 20 may comprise different displays, buttons, touchscreens, keyboards or other human machine interface means.

The image frames captured by the camera may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the subject. Thereby, an image pixel may correspond to one photosensitive element of a photo-detector and its (analog or digital) output or may be determined based on a combination (e.g. through binning) of a plurality of the photosensitive elements.

The system 10 further comprises two light sources 22, 24. A first light source 22, such as a lamp, is provided for illuminating a region of interest 26, such as the skin of the patient's face (e.g. outer part of the ear) with light in a first wavelength range to obtain reflected light from said region of interest 26 which is detected by the camera. A second light source 24, such as an LED or other (preferably miniature) light source, is provided for transmitting light through at least part of the region interest 26, in particular the outer part of the ear, in a second wavelength range to obtain transmitted light.

The first light source 22 emits light in at least a first wavelength range, e.g. in the wavelength range, which includes green light, and the second light source 24 emits light in at least a second wavelength range different from the first wavelength range, e.g. in the wavelength range of red and/or infrared light. The amplitude of green PPG pulsatility in reflective mode is much larger than red or IR PPG pulsatility in reflective mode. Pulsatility of red and IR PPG pulsatility in transmissive mode is larger than in the reflective mode. Therefore, this embodiment benefits from the combination of large green PPG pulsatility in reflective mode and large PPG pulsatility of IR or red in transmissive mode. However, the present disclosure not limited only to this distribution of wavelengths between reflective and transmissive modes.

In another embodiment no dedicated first light source is provided, but ambient light is used for illumination of the subject in the reflective mode. From the reflective light only light in the desired wavelength range (e.g. green light) is detected and/or evaluated. Thus, also in this embodiment the light portion that is evaluated from the reflective light and the light portion that is evaluated from the transmitted light are in different wavelength ranges.

The transmission of light by the second light source 24 and the illumination of the region of interest with light by the first light source are at least temporarily simultaneous. For instance, the first light source 22 may continuously illuminate the region of interest 26, while the second light source 24 may transmit light through the ear periodically only at certain time intervals, as will be explained in more detail below.

A system 10 as illustrated in FIG. 1 may, e.g., be located in a hospital, healthcare facility, elderly care facility or the like. Apart from the monitoring of patients, the present disclosure may also be applied in other fields such as neonate monitoring, general surveillance applications, security monitoring or so-called live style environments, such as fitness equipment, or the like. The uni- or bidirectional communication between the device 12, the light sources 22, 24 and the interface 20 may work via a wireless or wired communication interface, whereby it is to be noted that one or both of the light sources 22, 24 may also be configured to operate stand-alone and without communication with the device 12.

Figure 2:
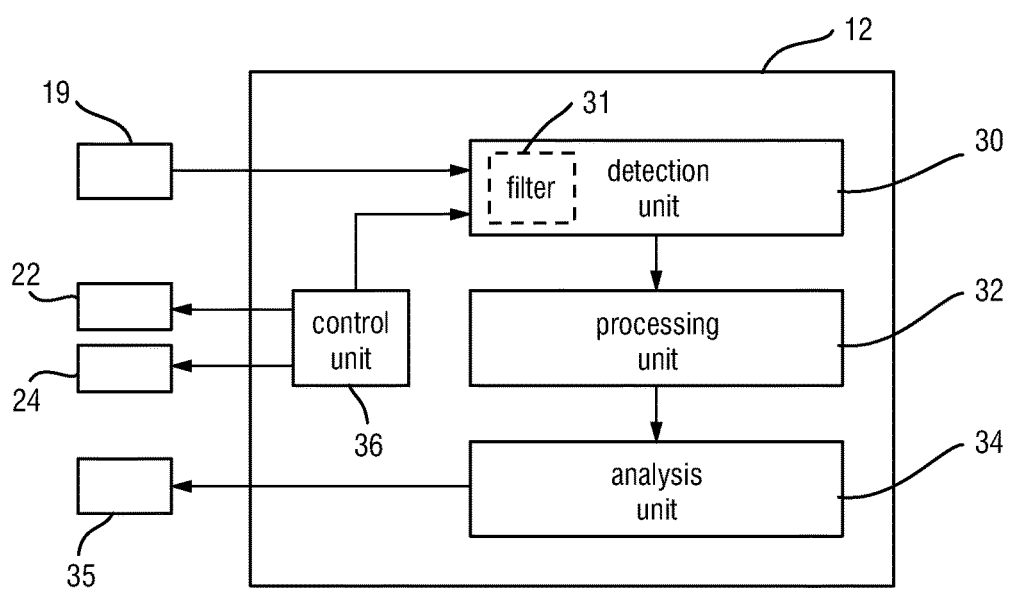
FIG. 2 shows schematic diagram of a device according to the present disclosure.

FIG. 2 shows a more detailed schematic illustration of an embodiment of the device 12 according to the present disclosure. The device 12 comprises a detection unit 30, e.g. a camera, for contactless detection of light in at least two different wavelength ranges from a region of interest of a subject based on a first light portion reflected from said region of interest in response to illumination by a first light source 22 in a first wavelength range and a second light portion transmitted through said region interest in response to illumination by a second light source 24 in a second wavelength range different from said first wavelength range. Further, a processing unit 32, e.g. a processor, is provided for deriving PPG signals from the detected light 19 (comprising the first and second light portions) for said at least two different wavelength ranges. The way to obtain PPG signals from detected light, e.g. from images of a region of interest, is generally known in the art, e.g. from the above cited documents, and will not be explained in more detail here. Still further, an analysis unit 34 is provided for deriving a desired vital sign 35 from the PPG signals for at least two different wavelength ranges. Also this step is generally known in the art, e.g. from the above cited documents, and will not be explained in more detail here.

Preferably, the device 12 further comprises a control unit 36 for controlling said first light source 22, said second light source 24 and/or said detection unit 30 to synchronize two or more of them with each other. The control unit 36 may further be configured to control said first light source 22 to emit light in said first wavelength range and/or said second light source 24 to emit light in said second wavelength range, for instance to exclusively or alternately emit light in the red or infrared wavelength range.

Figure 3:
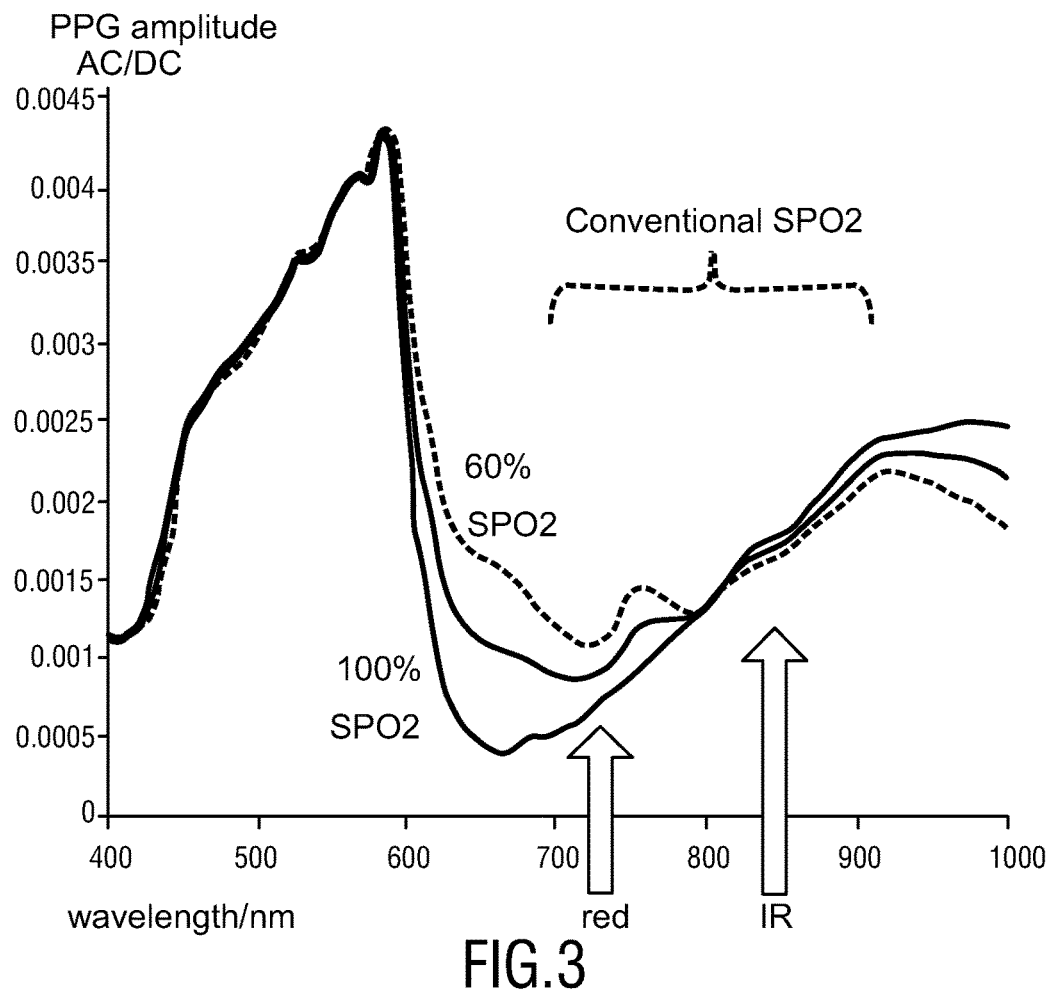
FIG. 3 shows a graph illustrating the selection of wavelengths of a dedicated illumination for SPO2 measurement.

This is illustrated in the diagram shown in FIG. 3, which illustrates an exemplary, non-limiting selection of wavelengths of a dedicated illumination for SPO2 measurement, particularly the dependency of PPG amplitude (AC/DC) for oxygenated (100% SpO2) and low oxygenated (60% SpO2) arterial blood. As shown, the second light source 24 can emit a light with at least one narrow spectrum band in the range >700 nm for extraction of a heart rate signal. In case SpO2 should be measured, the second light source 24 allows emitting of light in at least two wavelength ranges: 650 nm-750 nm (red light) and >800 nm (infrared light). The light can be emitted by the second light source 24 either sequentially in time or simultaneously. The wavelengths emitted by the second light source 24 are selected according to the graph shown in FIG. 3.

There are a number of further embodiments, which are based on different combinations of detection unit and light sources and/or different control schemes.

In a rather simple embodiment the system 10 includes one monochrome camera as detection unit and a second light source emitting light in the IR range at one wavelength with a narrow band. In this case the first light is ambient light (at least its visible part of the spectrum). In this case the system measures the combination of PPG pulsatility generated by reflected ambient light and PPG pulsatility generated by transmitted IR from a dedicated light source. That can be actually a main, simplest embodiment. In this embodiment no dedicated first light source is provided, but ambient light (e.g. sun light and/or room light) is used for illumination of the subject in the reflective mode, and from the reflective light only light in the desired wavelength range (e.g. green light) is detected and/or evaluated, for instance by use of filters as mentioned above.

Figure 4:
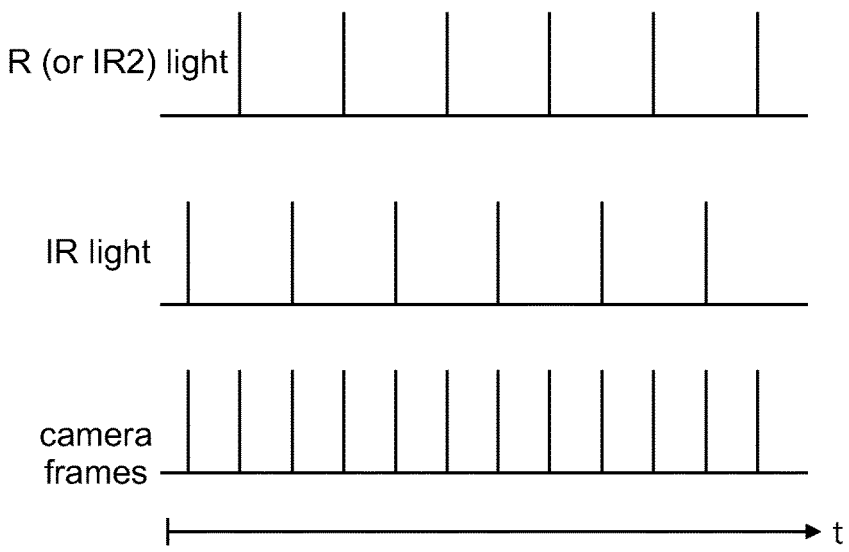
FIG. 4 shows a diagram illustrating a first example of the alignment of image frame detection with illumination.

In another embodiment the system comprises one monochrome camera and a second light source emitting light in a red and IR range with at least two wavelengths (preferably with a narrow band) sequentially in time. Frame capturing of a camera is synchronized in time with the second light source in a way that adjacent image frames are captured at different wavelengths of the second light source, as depicted on FIG. 4. FIG. 4 shows a time diagram of the light emission by the second light source 22 and the alignment of said illumination in the IR and red (or a second infrared, IR2) range with the capturing of image frames by the monochrome camera.

In still another embodiment the system comprises a camera with at least two optical filters 31 (shown as optional element with dotted lines in FIG. 2) in the red and IR range in front of the camera's image sensor, which correspond to the narrow bands of the illumination wavelengths of the second light source 22. In this case the light in at least two wavelength bands is preferably emitted continuously.

In still another embodiment the system comprises a camera, which includes three filters in green, red and IR range in front of the camera's image sensor (filters can be arranged similarly to RGB filters of a conventional color camera). Frame capturing of the camera would be synchronized with the second light source 22 operating in red and IR range. This embodiment allows an acquisition of a PPG signal in transmissive and reflective modes simultaneously. The transmissive mode operates in the red and IR range, while the reflective mode operates in the green, red and IR ranges. In an embodiment a combination of a conventional (e.g. finger pulse) sensor of transmissive PPG, which operates at red and IR wavelengths sequentially, and a reflective green PPG. For the reflective mode there can be either ambient or dedicated light, which contains green in the spectrum. For the transmissive mode there will be dedicated light with a spectrum of 650-1000 nm.

Figure 5:
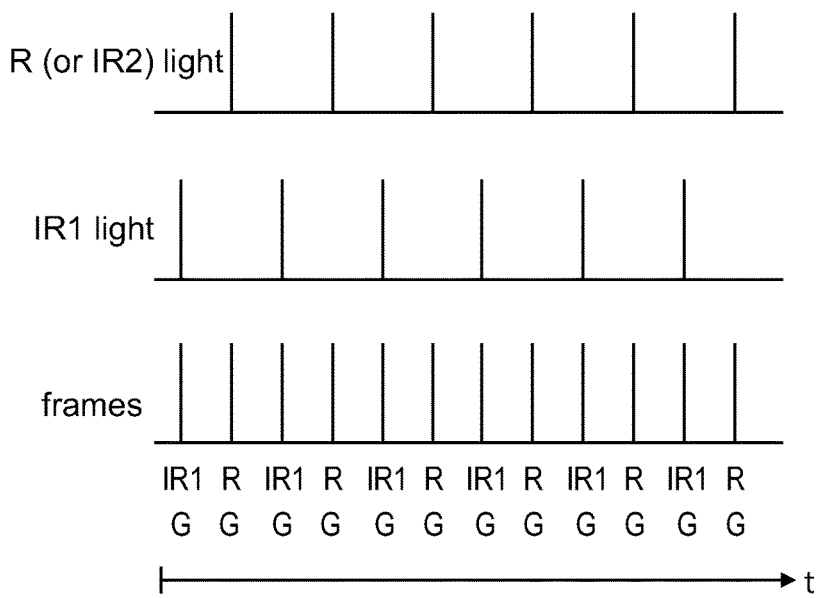
FIG. 5 shows a diagram illustrating a second example of the alignment of image frame detection with illumination.

FIG. 5 shows an example of the time synchronization of a camera and the second light source. In this example the second light source emits light with the red (R) (or second infrared, IR2) and first infrared (IR1) wavelengths sequentially in time. The light of the first light is not explicitly shown, but this may be ambient light that is present all the time and covers the whole visible spectrum including green light. That allows improvement of the robustness of the PPG signal acquisition compared to the use of ambient illumination (in the range of red, IR1, IR2), by comparing the corresponding sensor data for each of the red (or IR2) and IR1 wavelengths with and without second illumination from the second light source. The (motion compensated) difference between adjacent frames for each of red (or IR2) and IR1 channels provides an estimation of the second light portion only (without the contribution of ambient illumination). Hereby, motion compensation is e.g. achieved by processing pixels along estimated motion vectors, like in any motion compensation video processing algorithm.

Moreover, sequential switching of the second light source on and off allows an acquisition of reflective PPG, when a dedicated illumination is off. Thus, the system in this embodiment combines a transmissive PPG in channels R (or IR2) and IR1, with reflective PPG in channels green (G), red (or IR2) and IR1. In another embodiment, reflective light in other wavelength ranges, such as the blue and green wavelength range, and transmissive light in the reflective wavelength range may be evaluated if necessary and/or favorable for the respective application and derivation of a desired vital sign.

There are many other embodiments for combination of the transmissive PPG with a dedicated illumination and reflective PPG with ambient illumination or illumination from another dedicated light source.

A preferred embodiment uses a second light source for dedicated illumination that is placed behind a subject's ear (e.g. like a hearing aid), while a camera is located in front of the subject's face. Frame capturing of this camera is synchronized with the second light source, thus acquiring both transmissive PPG signal (with a light emitted from the second light source) and reflective PPG signal (with ambient light or light from a first light source).

Figure 6:
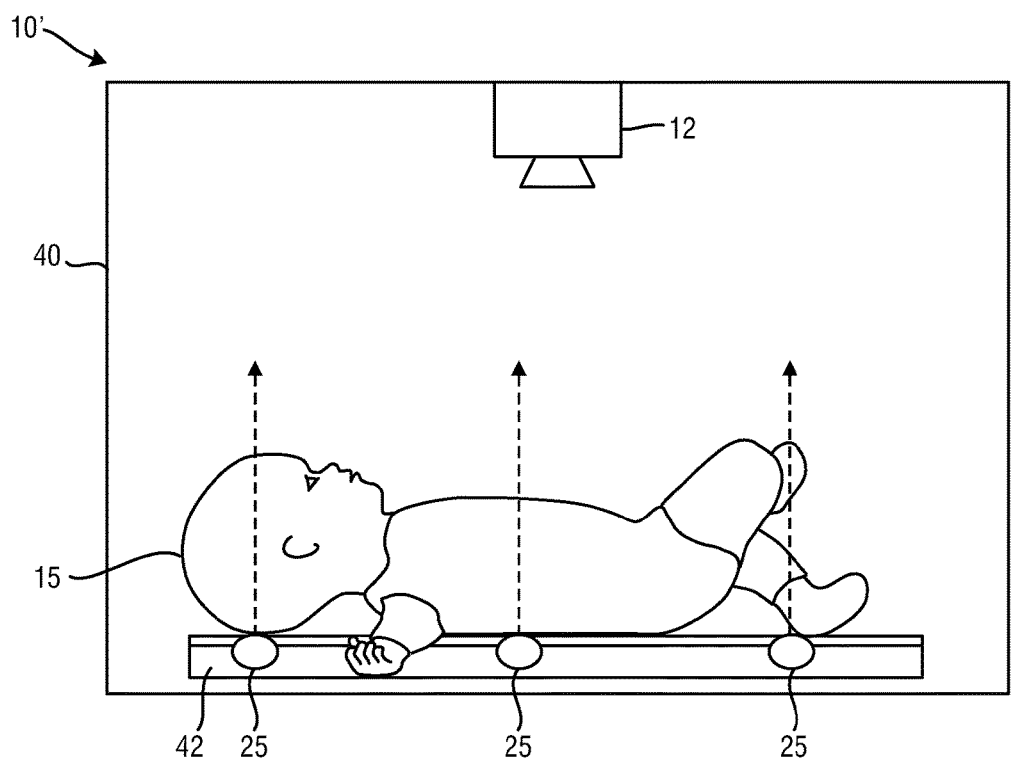
FIG. 6 shows a schematic diagram of another embodiment of a system according to the present disclosure and FIG. 7 shows a schematic diagram of an embodiment of a wearable light source device.

Another embodiment of proposed system 10' is depicted in FIG. 6. In this embodiment the second light source comprises a plurality (here 3) light source elements 25, e.g. LEDs or lamps, which are embedded in the mattress 42 of an NICU 40, while a device 12 including a camera is positioned above a baby 15 and acquires both transmissive and reflective light, from which the PPG signals for the derivation of one or more vital signs are obtained as explained above.

It should be noted that the elements of the device 12 may not necessarily combined into a single entity or housing, but may also be arranged in a distributed manner. For instance, the processing unit 32 and the analysis unit 34 (and also the control unit 36) may also be arranged separate from the camera 30, e.g. within the interface 20 or in a separate computer.

Figure 7:
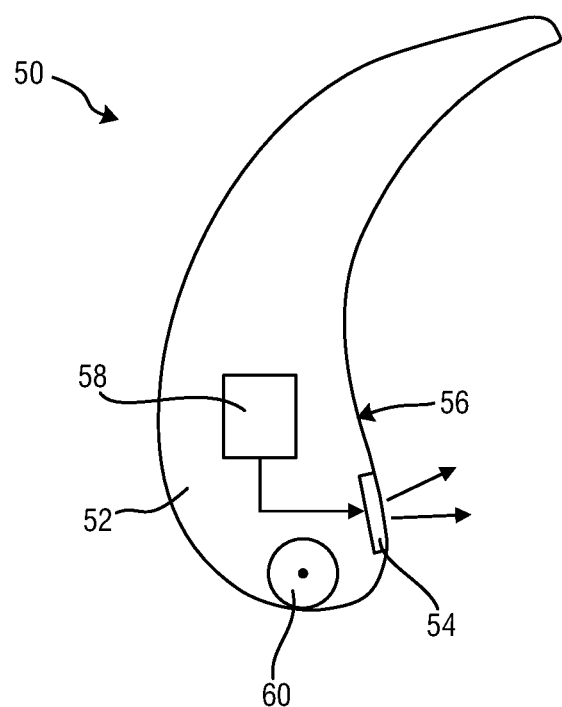

FIG. 7 shows a schematic diagram of an embodiment of a wearable light source device 50 according to the present invention. Said wearable light source device 50 is preferably used as second light source 24 shown in FIG. 1.

The wearable light source device 50 comprises a holder 52 for arranging the wearable light source device to a portion of a subject's body, in this embodiment behind a person's ear, in which case the holder has e.g. the form of a hearing aid. A light source 54, e.g. an LED, for emitting light is mounted in or at the holder 52 such that the emitted light is transmitted through a region interest of the subject for illuminating the region of interest to obtain transmitted light. In this embodiment the light source 54 is arranged at the surface 56 of the holder 52 that faces the rear side of the ear lobe so that the light is transmitted through the ear lobe and the transmitted light can be seen and captured from the front side of the ear lobe.

A control input 58 is provided for receiving control information, e.g. from the control unit 36 shown in FIG. 2, for controlling the light source 54 in a way as described above. For instance, in an embodiment the light source is controlled such that frame capturing of the camera 12 is synchronized in time with the light source 54 in a way that adjacent image frames are captured at different wavelengths of the light source 54. Preferably, said control input 58 is configured for wirelessly receiving control information, e.g. via Bluetooth, WLAN, Zigbee, etc.

Further, preferably a power source 60, such as a battery is provided in order to avoid any cabling and ensure self-sustaining operation of the wearable light source device 50.

In summary, the present disclosure provides substantial advantages over the existing SpO2 measurement methods using a clamping sensor (clamped to the finger or earlobe) or a camera (using rPPG). In particular, an SpO2 clamping device is sensitive to motion and disturbances caused by ambient light. The additional (second) light source provided according to the present disclosure may be a battery supplied LED which is placed behind the ear. It may be wireless device and does not need to be "clamped". Further, the quality of the SpO2 measurement (in terms of SNR) of the SpO2 camera measurement is enhanced.

By way of example, the present disclosure can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. The present disclosure can particularly be used for rapid and reliable pulse detection of a critical patient, for instance during automated CPR (cardiopulmonary resuscitation). The system can be used for monitoring of vital signs of neonates as well. In general, the present disclosure allows both spot-check and continuous monitoring.

While the disclosure has been illustrated and described in detail in the drawings and foregoing description, such illustration and description are to be considered illustrative or exemplary and not restrictive; the disclosure is not limited to the disclosed embodiments. Other variations to the disclosed embodiments can be understood and effected by those skilled in the art in practicing the claimed disclosure, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device for determining vital signs of a subject, the device comprising:
   a first light source configured to emit light of a first wavelength range, the first light source being remote from the subject;
   a second light source configured to emit light of a second different wavelength range, the second light source being operatively connected with the subject;
   a detection unit configured for contactless detection of light in the first and second different wavelength ranges from a region of interest of a subject, wherein said detection unit is configured to:
      detect a first light portion in the first wavelength range from light reflected from said region of interest; and;
      detect a second light portion in the second wavelength range from light transmitted through said region of interest, wherein said detection unit is configured to detect said first light portion and said second light portion simultaneously in response to illuminations that are at least temporally simultaneous,
   one or more computer processors programmed to:
      derive plethysmography (PPG) signals from the detected light for said at least two different wavelength ranges, and
      derive a desired vital sign from the PPG signals for the first and second different wavelength ranges.

2. The device as claimed in claim 1, wherein the one or more computer processors are further programmed to:
   control said first light source, said second light source and/or said detection unit to synchronize two or more of them with each other.

3. The device as claimed in claim 1, wherein the one or more computer processors are further programmed to:
   control said first light source to emit light in said first wavelength range and/or said second light source to emit light in said second wavelength range.

4. The device as claimed in claim 3, wherein the one or more computer processors are further programmed to:
   control said second light source to exclusively or alternately emit light in the red or infrared wavelength range.

5. The device as claimed in claim 1, wherein said detection unit comprises:
   one or more optical filters configured to filter light at said first and second wavelength ranges out of the detected light; and
   at least one electronic processor programmed to detect the light illuminated from each of the first and second light sources.

6. The device as claimed in claim 1, wherein the one or more computer processors are further programmed to:
   control said second light source to continuously emit light in said second wavelength range.

7. The device as claimed in claim 1, wherein the one or more computer processors are further programmed to:
   combine said PPG signals for at least two different wavelength ranges; and
   derive a desired vital sign from the combined PPG signals.

8. The device as claimed in claim 1,
   wherein said detection unit includes a camera configured to obtain a set of image frames of the region of interest.

9. The device as claimed in claim 6, wherein the one or more computer processors are further programmed to:

control said second light source to continuously emit light in the red and infrared wavelength range.

10. The device as claimed in claim 1, wherein the second light source is configured to transmit light through a region interest of a subject for illuminating the region of interest to obtain transmitted light, wherein the transmission of light and the illumination of the subject by light to obtain reflected light are at least temporally simultaneous.

11. The device as claimed in claim 1,
wherein the first light source is configured to illuminate the region of interest with light in said first wavelength range to obtain reflected light from said region of interest.

12. The device as claimed in claim 10,
wherein the second light source is configured for being arranged behind an ear or on one side of a hand of a person.

13. The device as claimed in claim 10,
further comprising a device having a mattress, wherein said second light source comprises a plurality of light elements arranged in said mattress.

14. The device as claimed in claim 13,
wherein said light source comprises a plurality of LEDs arranged in mattress.

15. A method for determining vital signs of a subject, the method comprising:
with a first light source remote from the subject, emitting light of a first wavelength range;
with a second light source operatively connected with the subject, emitting light of a second wavelength range;
with a detection unit, contactlessly detecting light in the first and second different wavelength ranges from a region of interest of a subject, wherein a first light portion is detected in the first wavelength range from light reflected from said region of interest and a second light portion is detected in the second wavelength range from light transmitted through said region interest, wherein said first light portion and said second light portion are detected simultaneously in response to illuminations that are at least temporarily simultaneous,
with a processing unit, deriving plethysmography signals from the detected light for said at least two different wavelength ranges, and
with an analysis unit, deriving a desired vital sign from the PPG signals for the first and second different wavelength ranges.

16. A method for determining a desired vital sign of a neonate in a neonatal care unit, the method comprising:
with a first light source remote from the neonate, emitting light of a first wavelength range;
with a second light source positioned in a bottom layer of the neonatal care unit, emitting light of a second wavelength range;
with a detection unit, contactlessly detecting light in the first and second different wavelength ranges from a region of interest of the subject, wherein a first light portion is detected in the first wavelength range from light reflected from said region of interest and a second light portion is detected in the second wavelength range from light transmitted through said region interest, wherein said first light portion and said second light portion are detected simultaneously in response to illuminations that are at least temporarily simultaneous,
with a processing unit, deriving plethysmography signals from the detected light for said at least two different wavelength ranges, and
with an analysis unit, deriving the desired vital sign from the PPG signals for at least two different wavelength ranges.

17. The device as claimed in claim 1, comprising:
a holder configured to position the first and second light sources to a portion of a subject's body.

18. The device as claimed in claim 17, wherein the one or more computer processors are programmed to:
wirelessly transmit control information to the detection unit; and
receiving the detected light signals from the detection unit.

19. The device as claimed in claim 1, wherein the one or more computer processors are further programmed to:
control a display device to display the derived desired vital sign.

20. The device as claimed in claim 1, wherein:
the first light source is configured to emit light in a red wavelength range; and
the second light source is configured to emit light in an infrared wavelength range.

* * * * *